(12) United States Patent
Severin et al.

(10) Patent No.: US 8,204,588 B2
(45) Date of Patent: Jun. 19, 2012

(54) SYSTEM AND METHOD FOR TRANSMITTING AND ACTIVATING A PLURALITY OF CONTROL DATA

(75) Inventors: Thomas Severin, Berlin (DE); Joern Bungartz, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 987 days.

(21) Appl. No.: 12/168,251

(22) Filed: Jul. 7, 2008

(65) Prior Publication Data

US 2009/0054937 A1 Feb. 26, 2009

(30) Foreign Application Priority Data

Aug. 24, 2007 (DE) .......................... 10 2007 040 038

(51) Int. Cl.
*A61N 1/39* (2006.01)
(52) U.S. Cl. ............. 607/5; 607/1; 607/2; 607/4; 607/9; 607/27; 607/30; 607/32; 607/60; 607/115; 128/920; 128/923; 600/300; 600/301; 600/508; 600/509
(58) Field of Classification Search ................ 607/1–2, 607/4–5, 9, 27, 30, 32, 60, 115; 128/920, 128/923; 600/300–301, 508–509
See application file for complete search history.

(56) References Cited

U.S. PATENT DOCUMENTS

| | | | |
|---|---|---|---|
| 4,625,730 A | 12/1986 | Fountain et al. | |
| 5,342,408 A | 8/1994 | deCoriolis et al. | |
| 6,443,891 B1 | 9/2002 | Grevious | |
| 2005/0027329 A1 | 2/2005 | Holmquist et al. | |

FOREIGN PATENT DOCUMENTS

| | | |
|---|---|---|
| DE | 693 31 875 | 11/2002 |
| EP | 0607638 | 7/1997 |
| EP | 13 22 217 B1 | 7/2003 |

*Primary Examiner* — Carl H Layno
*Assistant Examiner* — Deborah Malamud
(74) *Attorney, Agent, or Firm* — Craig A. Fieschko, Esq.; DeWitt, Ross & Stevens, S.C.

(57) ABSTRACT

A cardiac pacemaker, defibrillator, or other programmable medical device (25) includes a source unit (15) and a collection unit (20). The source unit (15) has a check data unit (40) generating at least one check datum for control data for the medical device (25), and a transmitting unit (45) transmitting the control data and the check datum to the collection unit (20). The collection unit (20) has a storage unit (65) storing the control data, a check unit (70) checking the integrity of the control data using the check datum, and a transmitting unit (75) transmitting the control data to a programmable control unit (80) of the medical device (25) only if the integrity of the control data is established by the check unit (70). The control unit (80) of the medical device (25) controls the functions of the medical device (20) on the basis of the transmitted control data.

17 Claims, 4 Drawing Sheets

SYSTEM AND METHOD FOR TRANSMITTING AND ACTIVATING A PLURALITY OF CONTROL DATA

FIELD OF THE INVENTION

The present invention relates to a system and a method for transmitting and activating a control data for a programmable personal medical device, in particular for an implantable medical device such as a cardiac pacemaker, defibrillator, or the like. In addition, the present invention relates to such a medical device and a source unit for control data.

BACKGROUND OF THE INVENTION

A medical device such as a cardiac pacemaker typically receives new control data several times during its operation, with the control data including matters such as changes to the operating parameters of the cardiac pacemaker, software or firmware updates or commands for the cardiac pacemaker, etc. When programming an implant such as a cardiac pacemaker, a programming session may involve the alteration of some parameters and the issuance of associated commands to the implant, such as a request to restart statistics or to begin detection of patient data, and the transmission of the parameters and commands to the implant.

When a clinical programmer programs the implant in a clinic, a control datum may be transmitted within a few seconds to the implant, with control data being transmitted to the implant in succession. When control data are remotely programmed and transmitted to the implant, the transmission may take as long as several days. In any event, control data are transmitted in succession, i.e., sequentially.

As more control data are to be transmitted in sequence and as the transmission grows longer, the more probable it is that at least one control datum will be transmitted incorrectly or incompletely. During a long transmission, an interruption of the transmission by a loss of connection can occur. In addition, during such a transmission, a chronological or logical assignment between different items of data may be lost. The control data thus arrive incomplete or corrupted at the implant, which may result in a malfunction of the implant upon an implementation/execution of the control data (e.g., acceptance of the operating parameters or overriding of the firmware). When firmware is updated via remote programming, the problem additionally results that many reprogrammings must be executed, with only one containing the new implant control software. All reprogrammings connected with the update must become active jointly. If all parts are not provided in the implant, the reprogramming may not occur.

SUMMARY OF THE INVENTION

The invention seeks to provide a system and a method for executing complete and secure transmission of control data, thereby avoiding the problems described above.

A preferred version of the invention involves a system for transmitting control data for a programmable personal medical device, in particular an implantable medical device, such as a cardiac pacemaker, defibrillator, or the like, having a source unit, a collection unit, and a medical device. The source unit has a data set unit for generating a control data set having a plurality of control data, a check data unit for generating at least one check datum for the control data set, and a transmitting unit for transmitting the control data set and check datum to the collection unit. The collection unit has a receiving unit for receiving the control data set and the check datum, a storage unit for storing the control data set and/or the control data of the control data set, a check unit for checking the integrity of the control data set using the check datum, and a transmitting unit for transmitting the control data to a programmable control unit of the medical device. The medical device has a programmable control unit for controlling functions of the medical device on the basis of the control data. The collection unit is implemented to transmit the control data to the control unit of the medical device only if the integrity of the control data set is established by the check unit. The control unit of the medical device is implemented to execute the control of functions of the medical device on the basis of the control data received from the collection unit.

The invention also encompasses a method for transmitting control data for a programmable personal medical device, in particular an implantable medical device such as a cardiac pacemaker, defibrillator, or the like, having the following steps:
  generating a control data set having a plurality of control data,
  generating at least one check datum for the control data set, and
  transmitting control data set and check datum to a collection unit,
  receiving the control data set,
  storing the control data set and/or the control data of the control data set,
  receiving the check datum,
  checking the integrity of the control data set using the control datum,
  transmitting the control data to a programmable control unit of the medical device, and
  executing a control of functions of the medical device on the basis of the control data received from the collection unit,
wherein the step of transmitting the control data to the programmable control unit only occurs if the integrity of the control data set is established during the checking.

The invention further encompasses a source unit and a personal programmable medical device. The source unit is used to transmit control data for a programmable personal medical device, in particular an implantable medical device such as a cardiac pacemaker, defibrillator, or the like, and includes a data set unit for generating a control data set having a plurality of control data, a check data unit for generating at least one check datum usable for an integrity check of the control data set, and a transmitting unit for transmitting control data set and check datum to a collection unit.

The programmable personal medical device is particularly an implantable medical device such as a cardiac pacemaker, defibrillator, or the like, and includes a collection unit and a programmable control unit, the collection unit having a receiving unit for receiving a control data set comprising control data and a check datum assigned to the control data set, a storage unit for storing the control data set and/or the control data of the control data set, a check unit for checking an integrity of the control data set using the check datum, and a transmitting unit for transmitting the control data to the programmable control unit of the medical device. The programmable control unit is provided for controlling functions of the medical device on the basis of control data. The collection unit is implemented to transmit the control data to the control unit of the medical device only if the integrity of the control data set is established by the check unit, and the control unit of the medical device is implemented to execute the control of functions of the medical device on the basis of the control data received from the collection unit.

The invention is based on the insight that in the event of a plurality of associated control data, the use of this control data may only be performed reliably if it is ensured in a suitable manner that all control data are also completely provided. The implant may execute the changes at one stroke if and only if an entire packet has been received. It is important for the safety and reliability of the implementation of the control data that either all changes are executed together, or none at all.

In one version of the invention, the medical device is an active medical implant. Special safety requirements, which are fulfilled by the present invention, exist for the operational safety in particular for an active medical implant.

In one version of the invention, the medical device is an implantable cardiac pacemaker or defibrillator-cardioverter. Secure communication of programming data or firmware updates according to the invention is advantageous particularly during operation of a cardiac pacemaker or a defibrillator-cardioverter.

In one version of the invention, the source unit has a programming device for the preparation of control parameters as control data for the control unit. An operator may prepare control parameters for the control unit in a familiar way, using the programming device known to him, without the control parameters having to be transmitted once again separately to the source unit.

In one version of the invention, the source unit is implemented to provide a control program for the control unit as the control data, the source unit particularly having a server for providing the control program. If the source unit is equipped with a server, the source unit may be supplied easily with control data by setting a firmware update on the server, for example.

In one version of the invention, the control data have a control parameter and/or a control program. A control data set may have both control parameters and also control programs, also in combination. In particular, in a firmware update, altered control parameters may also be activated together with the update.

In one version of the invention, the control data include meta-control data for the control unit for using the control data during the control of functions of the medical device, in particular information in regard to a sequence, a chronological succession, and/or a duration of the use of the control data and/or information in regard to a condition for the use of the control data. In addition to the actual control data, information on the use of the control data is contained in the control data set, which allows greater flexibility of the system according to the invention and better response to operator wishes.

In one version of the invention, the medical device itself has a collection unit. The collection unit may be situated in the medical device itself, so that the medical device does not require an external collection unit.

In one version of the invention, a collection unit is situated separately from the medical device and may be coupled to the medical device via a data connection, in particular via a wireless data connection having low range, preferably according to a medical implant communication service specification, the collection unit preferably being situated in a patient device assigned to the medical device. The collection unit is provided outside the medical device and thus checks incoming control data sets independently of the medical device, the checked control data then being transmitted to the medical device.

It is also possible according to the invention that the collection unit itself in turn functions as a source unit for transmitting the control data to the medical device, the medical device then having a further collection unit itself. Different source and collection units may be provided in a cascade for different communication sections.

In one version of the invention, the system includes a combination unit having a receiving unit for receiving a first and a second control data set from a source unit, a storage unit for storing the first and the second control data sets and/or the control data of the first and/or second control data set, a check data unit for generating at least one combination check datum for a third control data set comprising the first and the second control data sets, and a transmitting unit for transmitting the third control data set and the combination check datum to the collection unit, the combination unit preferably also having a check unit for checking an integrity of the first and the second control data sets using a first and a second check datum received from the receiving unit, the combination unit being implemented only to transmit the third control data set to the collection unit if an integrity of the first and the second control data sets is established by the check unit. The combination unit includes both functionalities of a source unit and also a collection unit, so that different control data sets, for example, from different source units or in (chronological) succession from one source unit, may be combined into a combined control data set. The combination unit is represented as a type of collection unit in relation to a source unit, while it acts as a source unit in relation to a collection unit.

In one version of the invention, the check datum includes an identifier establishing an integral control data set, in particular a unique identifier, preferably a checksum and/or a hash value. The generation of a unique value from the control data set represents a simple way to identify and be able to check the control data set. Checksums or hash values which uniquely identify a control data set are especially advantageous, i.e., practically no other control data set results in the same hash value or the same checksum, so that an alteration of the control data set is recognized in any case. Non-unique check data may also be used, if the probability for incorrectly assumed integrity is small enough.

In one version of the invention, the check datum includes a control data set end signal to indicate a complete transmission of the control data set, preferably in combination with a control data set start signal. Upon a transmission of a signal indicating a start of the control data set and a signal indicating an end of the control data set, it may at least be assumed upon arrival of the control data set end signal that the connection has not been lost during the transmission, because otherwise the end signal would not have arrived. As soon as the end signal indicates the completeness of the control data set, the entire control data set may thus be processed as a whole.

In one version of the invention, the control data set end signal and the control data set start signal are each provided with an identifier, which allows an assignment of control data set start signal and control data set end signal to one another. An identification of the start and end signals is used for identification and allows, inter alia, different control data sets to be transmitted in parallel without the end and start signals being confused with one another.

In one version of the invention, the check unit is implemented to transmit a characterization of the control data set and/or the control data forming the control data set to the check data unit, the check data unit generating the check datum on the basis of the characterization and the transmitting unit being implemented for separate transmission of control data set and check datum. One possibility for checking the integrity according to the invention includes a query at the point which has output the control data set, the query appending the required information to the received control data set, so that a comparison between the control data set to be transmitted or transmitted and the received control data set is possible. A transmission of the check datum in the form of a confirmation of the completeness and correctness is performed on the basis of this comparison.

In one version of the invention, the source unit is implemented to generate and transmit a fourth data set and a fourth check datum having an urgency indicator after a transmission of the first control data set, the collection unit being implemented to interrupt the processing of the first control data set if the collection unit receives the fourth control data set having the urgency indicator. In this case, the transmission of a specially identified control data set, which may also contain a single control datum here, at least suspends the processing of prior control data sets, so that this special control data set may be processed as rapidly as possible in case of emergency and reach its goal, for example.

In one version of the invention, the collection unit is implemented to abort the processing as an interruption and empty of the storage unit of control data of the first control data set. Upon an interruption of the processing, the processing of the control data set may not only be suspended as a whole, but rather completely aborted, the received control data being removed from the storage unit.

In one version of the invention, the collection unit is implemented to reassume the processing of the control data set after a processing of the fourth control data set, the control unit being implemented to retain the received first control data set and/or the received control data of the first control data set in addition to the fourth control data set and/or the control data of the fourth control data set. Alternatively (or additionally) to the abort described above, the system is also capable of reassuming the processing in the event of an interruption after processing the interrupting (emergency) control data set.

Further advantageous versions of the invention result in particular by combination of features of the claims and from the following description of preferred exemplary versions of the invention.

BRIEF DESCRIPTION OF THE DRAWINGS

The invention is explained in greater detail hereafter on the basis of preferred exemplary versions with reference to the appended figures. In the figures.

DETAILED DESCRIPTION OF THE INVENTION

Figure 1:
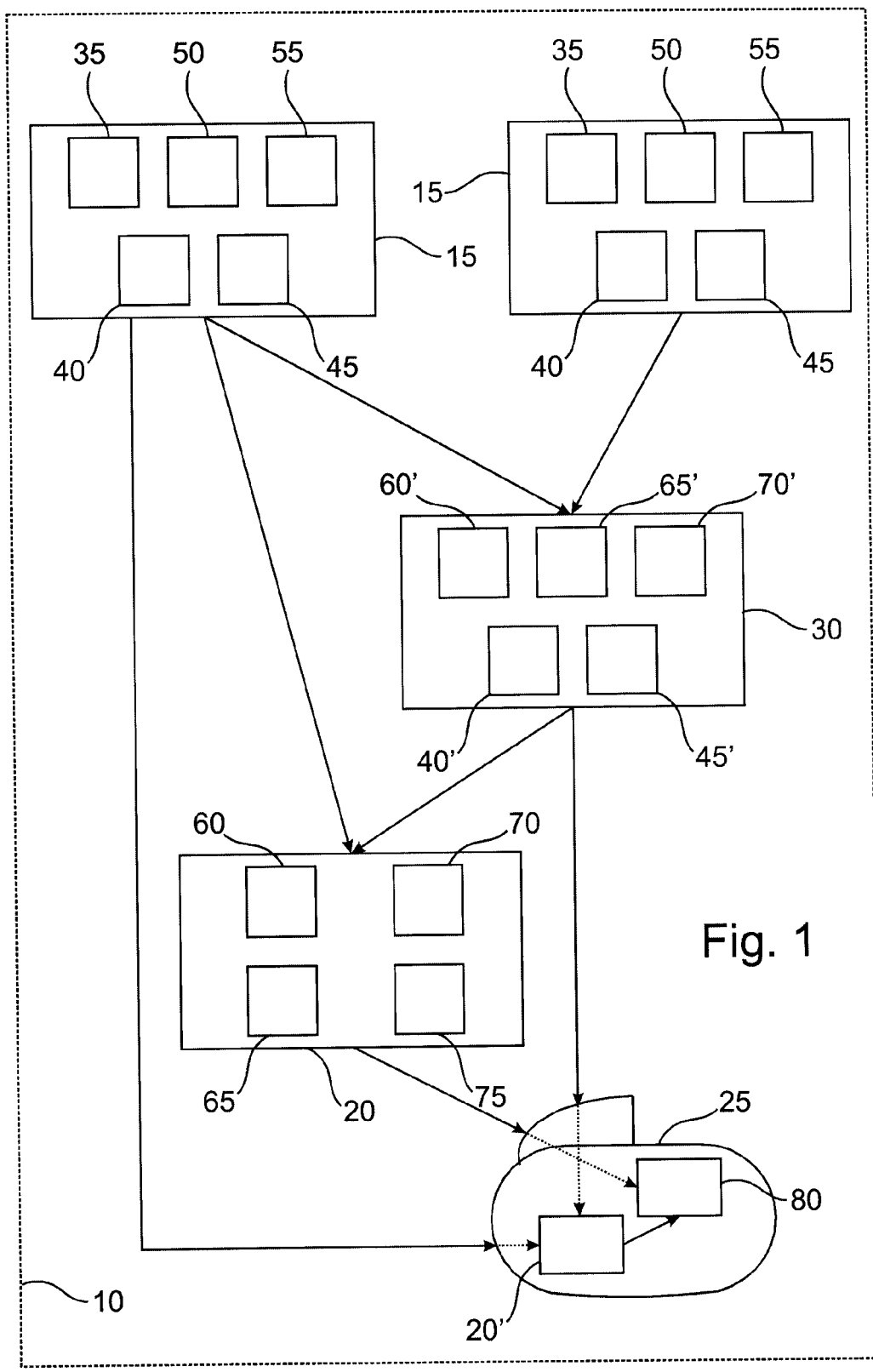
FIG. 1 shows a schematic illustration of an exemplary version of the invention.

FIG. 1 shows a schematic illustration of an exemplary version of the invention. The system 10 includes a first and a second source unit 15, a collection unit 20, an implant 25, and a combination unit 30.

The first and the second source unit 15 are constructed essentially identically, operate corresponding to one another, and each include a data set unit 35, a check data unit 40, a transmitting unit 45, a programming device 50, and a server 55. The collection unit 20 includes a receiving unit 60, a storage unit 65, a check unit 70, and a transmitting unit 75. The implant 25 includes a programmable control unit 80 and a separate collection unit 20', which is constructed and operates fundamentally like the foregoing collection unit 20. The combination unit 30 includes a receiving unit 60' similar to the receiving unit 60 of the collection unit 20, a storage unit 65' similar to the storage unit 65 of the collection unit 20, a check unit 70' similar to the check unit 70 of the collection unit 20, a check data unit 40' similar to the check data unit 40 of the source unit(s) 15, and a transmitting unit 45' similar to the transmitting unit 45 of the source unit(s) 15.

A physician prepares control data in the form of control parameters for the implant 25 using the programming device 50 of the source unit 15. An alternative to this preparation includes the provision of a control data set with a firmware update in the server 55 of the source unit 15. In any case, the prepared control data are compiled by the data set unit 35 into a control data set, for which the check data unit 40 prepares a checksum as the check datum. The control data set and the check datum are sent to the collection unit 20 via the transmitting unit 45. Alternatively, the control data set and the check datum may also be sent to the collection unit 20' of the implant 25 or to the combination unit 30.

The collection unit 20 receives the control data set and the check datum using the receiving unit 60 and stores the control data from the control data set in the storage unit 65. The check unit 70 of the collection unit 25 also generates a checksum of the control data set in a way which corresponds to that of the check data unit 40. If a comparison of the transmitted checksum to the checksum generated in the collection unit results in a correspondence, the integrity of the control data set is thus assumed. The control data are therefore transmitted to the control unit 80 of the implant 25, where they are implemented.

The combination unit 30 is designed to accept control data sets and check data from both source units 15 via the receiving unit 60'. The control data and/or control data sets are stored in the storage unit 65', the check unit 70' again generating checksums and performing a comparison. In case of a positive result, the control data sets recognized as complete and correct are combined into a joint control data set, a combination check datum for the combination control data set again being generated by the check data unit 40'. The combined control data set is transmitted with the combination check datum either to the collection unit 20 or directly to the implant 25 (more precisely its collection unit 20'), where the combination control data set and the combination check datum are handled like a control data set and a check datum of the source unit 15.

The implant 25 is equipped with a separate collection unit 20', so that it may also directly or indirectly receive control data sets and check data from a source unit 15 or a combination unit 30 and check them for integrity before they are implemented by the control unit 80.

Figure 2:
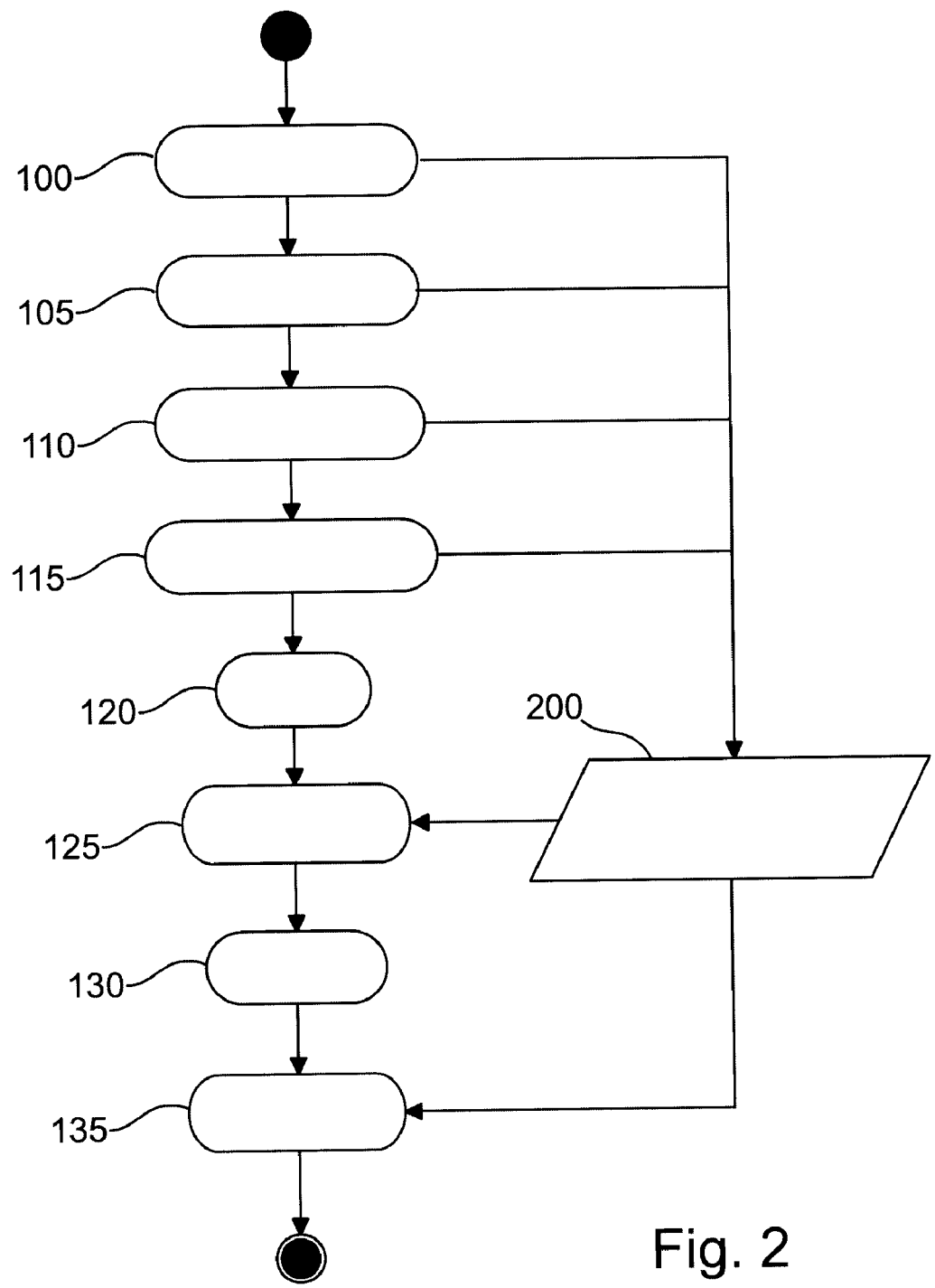
FIG. 2 schematically shows a sequence for preparing a control data set.

FIG. 2 schematically shows an exemplary sequence for preparing a control data set. In step 100, a control datum for a setting of a first parameter is generated (e.g., parameter 1→200). In step 105, a control datum for a setting of a second parameter is generated (e.g., parameter 2→50). In step 110, the setting for the second parameter is overwritten (e.g., parameter 2→100). In step 115, a control datum for a setting of a third parameter is generated (e.g., parameter 3→"OFF"). The particular control data are introduced upon their preparation and/or revision into the control data set 200, which then contains the control data having the desired settings. In step 120, the termination of the settings is initiated to initiate the transmission of the control data set. In step 125, the content of the control data set is displayed, so that the user may perform a confirmation in step 130. In step 135, the control data set is released for a transmission to an implant.

Figure 3A:
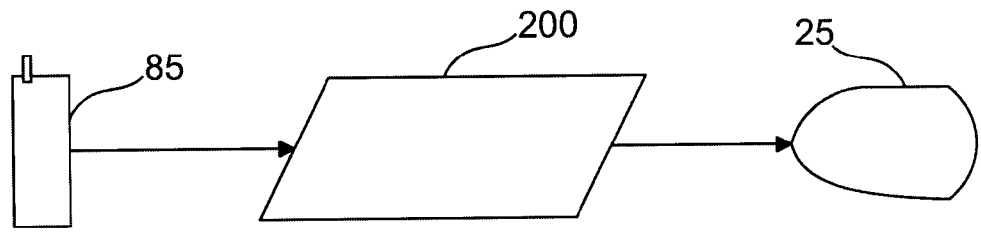
FIGS. 3a-3c show schematic sequences of an exemplary version of the invention.
Figure 3B:
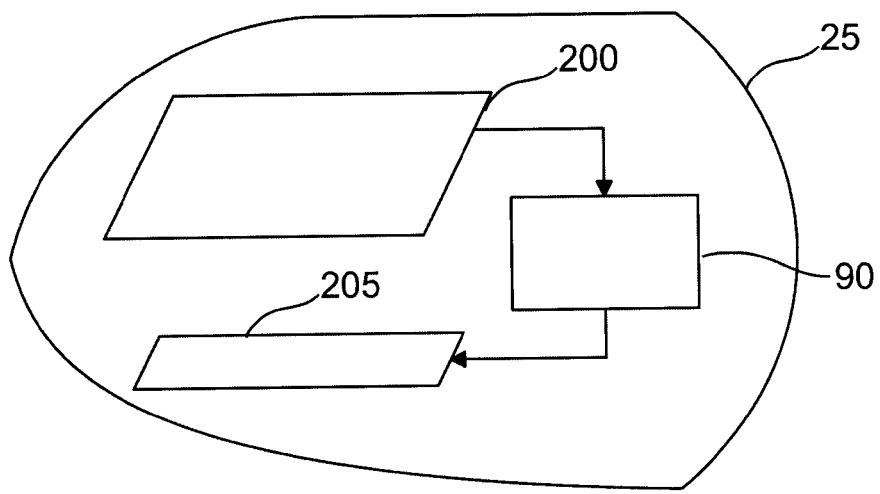
Figure 3C:
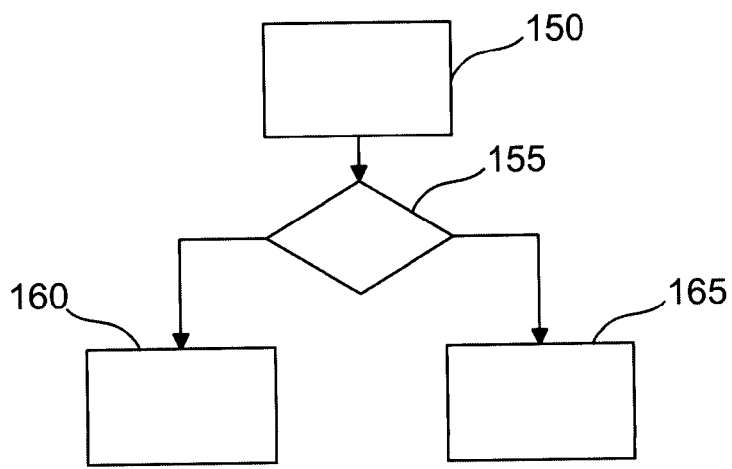

FIGS. 3a-3c show schematic sequences of an exemplary version of the invention. FIG. 3a shows that a control data set 200 is transmitted from a patient device 85, tuned to the implant 25, which serves as a relay station to the implant 25. In the implant 25, a checksum 205 is calculated from the control data set 200 by a correspondingly programmed CPU or computing unit 90 of the collection unit of the implant 25. In the event of a correspondence, which is established in step 155, the predetermined execution of all control data which were contained in the control data set 200 is performed, in step 160. If the checksums do not correspond, all control data of the control data set 200 are discarded in step 165.

Figure 4A:
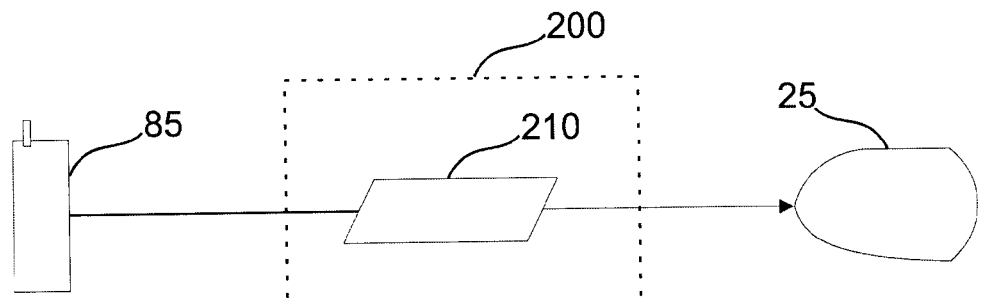
FIGS. 4a-4d show schematic sequences of another exemplary version of the invention.
Figure 4B:
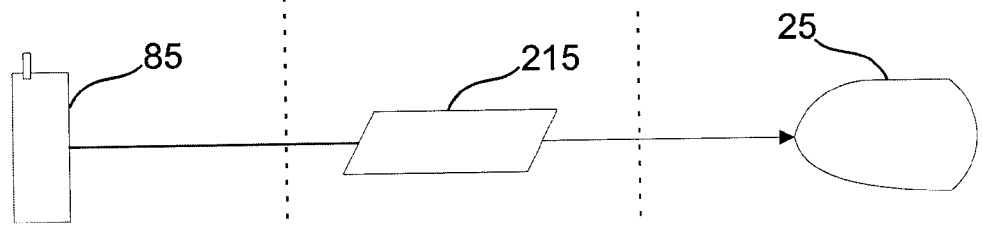
Figure 4C:
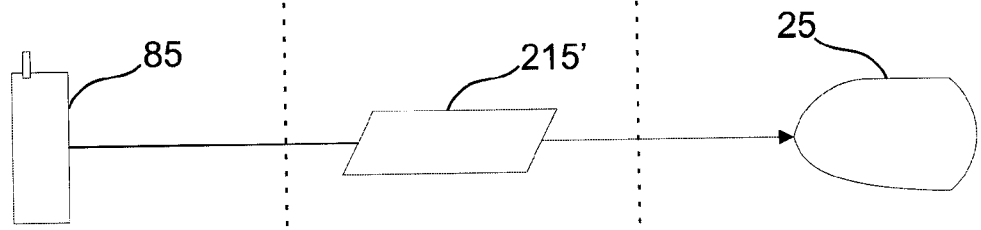
Figure 4D:
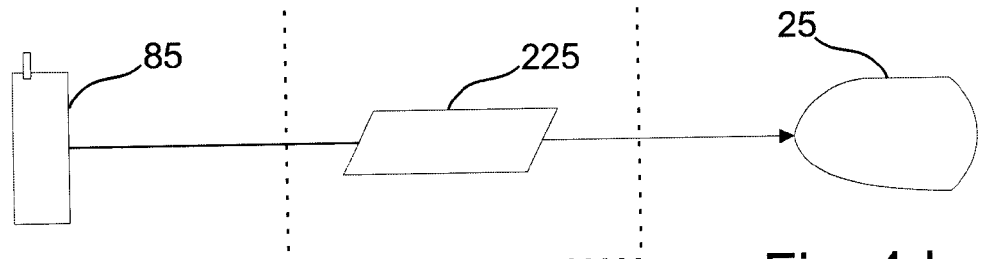

FIGS. 4a-4d show schematic sequences of another exemplary version of the invention. The relay station 85 (the patient device) has obtained a firmware update here and transmits it in smaller packets to the implant 25. For this purpose, the patient device 85 transmits a control data set start signal 210 to the implant 25 (FIG. 4a). It then transmits the firmware update together with further control data such as new control parameters to the implant 25 (FIGS. 4b, 4c) in packets 215, 215', whose size and number result through the communication protocol between implant 25 and patient device and the extent of the control data and/or the control data set (of the update). After all packets 215, 215" have been transmitted, the patient device 65 transmits a control data set end signal 225 to the implant 25 (FIG. 4d). Upon receiving the control data set end signal 225, the implant assumes that all control data of the control data set 200 have been completely received, because in the event of a communication breakdown between implant 25 and patient device 85, the control data set end signal would not have arrived. By generating the control data set start and end signals, the patient device 85 at least partially assumes the function of a check data unit and is thus also to be seen as a component of a source unit within the meaning of the invention.

Upon a transmission of a program (control data) to an implant by remote programming, according to one exemplary version of the invention, a home monitoring service center (HMSC) compiles a data packet having multiple individual changes as in a "shopping basket" and provides the packet with a secure checksum. The implant receives the packet and checks the integrity of the packet on the basis of the checksum. If the packet is intact (the checked checksums correspond), the individual changes contained therein are completely executed. If the packet is incomplete or damaged (the checksum is erroneous), the contained changes are completely discarded, because it cannot be known which individual control data could still possibly be executed in spite of the incompleteness.

A further exemplary version of the invention relates to the transmission of new firmware to the implant by remote programming. The HMSC sends new implant firmware to a patient device (also called a telex) tuned to the implant. The telex sends a "transaction start" command to the implant. The telex sends a firmware image divided into multiple individual packets to the implant. The telex sends a "transaction end" command to the implant. The implant checks the transmitted firmware on the basis of the checksum upon receipt of the "transaction end" command and activates the new firmware in the event of correctness. If the "transaction end" command is not received, the implant state does not change, and the received parts of the new firmware are discarded (preferably after passage of a specific deadline).

One exemplary version of the invention relates to an alteration of the implant program using a clinical programmer. On the programming device (programmer), an implant parameter was altered and the program transmitted. Various parameter blocks had to be altered concurrently. Either all alterations are to be executed or none of them. The parameter blocks "SensingBradyCommon" and "BradyModepage" were altered, which are in various positions in the implant. The command "accept program" is to be transmitted, which activates the changes. The command "restart statistics" is to be executed, because after the programming the statistics become inconsistent. The command "detection on" is to be transmitted. The four commands (the alteration of the parameter blocks and the three commands) are compiled into one block (control data set) and transmitted to the implant provided with a checksum. After the completed transmission of the block, the implant checks the checksum and aborts in the event of an erroneous checksum. The parameter blocks "SensingBradyCommon" and "BradyModepage" are assumed at the target position in the implant. The commands "accept program", "restart statistics", and "detection on" are executed. The implant transmits a completion acknowledgment to the programming device.

As an illustration of another exemplary version of the invention, upon transmission of new firmware to the implant by a clinical programmer, the control software of the implant is replaced by a newer version. In addition, the parameter settings are adapted to the new control software and also transmitted to the implant in addition to the new firmware. A firmware update lasts (for example) approximately 3 minutes. During the procedure, the old control software is to be active. After successful transmission, the new control software is activated together with the new parameters at one stroke. A total of (for example) 30 steps must be executed. All steps are transmitted by the programmer into a buffer memory of the implant. The new software and the parameter settings become active at one stroke in the implant with the last step "copy and activate", if the check of the check data of the transmission of the control data set having the firmware update and the new parameter settings indicates a complete and correctly received control data set.

The present invention allows the user to execute aftercare via remote programming in a familiar way. He may alter parameters, accept them in a "shopping basket", alter further parameters (e.g., on another GUI page), also accept them in the "shopping basket", set an instruction to restart the statistics in the "shopping basket", and trigger a transmission of the "shopping basket". The complex reprogrammings combined in the "shopping basket" then occur either completely or not at all. Intermediate states in the implant (half programmed, e.g., due to connection interruption or transmission error) are thus prevented.

The transmission of a (large and complex) parameter set may preferably be interrupted at any time, so that emergency commands may be transmitted and executed within a short time.

The described transmission method is generic. Programming may include a sequence of many small blocks and commands. The composition and sequence of the programming may be performed by changes on the HMSC program (remote programming) without altering the implant control software.

The invention claimed is:

1. A system (10) for transmitting control data for a programmable personal medical device (25), including a source unit (15), a collection unit (20), and a personal device (25),
   a. wherein the source unit (15) includes:
      (1) a data set unit (35) generating a control data set (200) having a plurality of control data, (2) a check data unit (40) generating at least one check datum usable for an integrity check of the control data set (200), and
(3) a transmitting unit (45) transmitting the control data set (200) and the check datum to the collection unit (20),
b. wherein the collection unit (20) includes:
(1) a receiving unit (60) receiving the control data set (200) and the check datum,
(2) a storage unit (65) storing the control data set (200) and/or the control data of the control data set (200),
(3) a check unit (70) checking the integrity of the control data set (200) using one or more check data, and
(4) a transmitting unit (75) transmitting the control data to a programmable control unit (80) of the personal device (25),
c. wherein the personal device (25):
(1) includes a programmable control unit (80) controlling functions of the personal device (25) in accordance with the control data,
(2) transmits the control data to the control unit (80) of the personal device (25) only if the integrity of the control data set (200) is established by the check unit (70), and
(3) executes, in the control unit (80), the control of functions of the personal device (20) on the basis of the control data received from the collection unit (20),
d. and further wherein:
(1) the source unit (15) is configured to generate and transmit a subsequent control data set and a subsequent check datum having an urgency indicator after a transmission of the control data set (200), and
(2) the collection unit (20) is configured to interrupt the processing of the control data set (200) if the collection unit (20) receives the subsequent control data set having the urgency indicator.

2. The system (10) of claim 1 wherein the personal device (25) is an active medical implant.

3. The system (10) of claim 2 wherein the personal device (25) is an implantable cardiac pacemaker or defibrillator-cardioverter.

4. The system (10) of claim 1 wherein the source unit (15) includes a programming device (50) wherein control data are prepared, the control data including control parameters for the control unit (80).

5. The system (10) of claim 1 wherein the source unit (15) includes a server (55) providing the control data, the control data including a control program for the control unit (80).

6. The system (10) of claim 1 wherein the control data include a control parameter and/or a control program.

7. The system (10) of claim 1 wherein the control data include meta-control data defining the control unit's (80) usage of the control data in the control of functions of the personal device (25), the meta-control data including at least one of information regarding:
a. a sequence for the use of the control data,
b. a chronological succession for the use of the control data,
c. a duration of the use of the control data, and
d. a condition for the use of the control data.

8. The system (10) of claim 1 wherein the personal device (25) includes the collection unit (20).

9. The system (10) of claim 1 wherein the check datum includes an identifier establishing an integral control data set (200), the identifier including at least one of:
a. a checksum, and
b. a hash value.

10. The system (10) of claim 1 wherein the check datum includes a control data set end signal (220) indicating a complete transmission of the control data set (200).

11. The system (10) of claim 10 wherein:
a. the check datum includes a control data set start signal (205) indicating a start of the transmission of the control data set (200),
b. the control data set end signal (220) and the control data set start signal (205) are each provided with an identifier assigning the control data set end signal (220) and the control data set start signal (205) to each other.

12. The system (10) of claim 1 wherein:
a. the check unit (70, 70') transmits a characterization of the control data set (200) and/or the control data forming the control data set to the check data unit (40, 40'),
b. the check data unit (40, 40') generates the check datum on the basis of the characterization, and
c. the transmitting unit (45, 45') separately transmits the control data set (200) and check datum.

13. The system (10) of claim 1 wherein the collection unit is configured to empty the storage unit (65) of control data of the control data set (200) upon interrupting the processing of the control data set (200).

14. The system (10) of claim 1 wherein
a. the collection unit (20) is configured to resume the processing of the control data set (200) after processing the subsequent control data set, and
b. the storage unit (65) is configured to retain the received control data set (200) and/or the received control data of the control data set (200) in addition to the subsequent control data set and/or the control data of the subsequent control data set.

15. A system (10) for transmitting control data for a programmable personal medical device (25), including a source unit (15), a collection unit (20), and a personal device (25),
a. wherein the source unit (15) includes:
(1) a data set unit (35) generating a control data set (200) containing control data,
(2) a check data unit (40) generating at least one check datum usable for an integrity check of the control data set (200), and
(3) a transmitting unit (45) transmitting the control data set (200) and the check datum to the collection unit (20),
b. wherein the collection unit (20):
(1) is situated separately from the personal device (25) within a patient device (85) assigned to the personal device (25), and
(2) is coupled to the personal device (25) via a wireless data connection,
(3) includes:
i. a receiving unit (60) receiving the control data set (200) and the check datum,
ii. a storage unit (65) storing the control data set (200) and/or the control data of the control data set (200),
iii. a check unit (70) checking the integrity of the control data set (200) using one or more check data, and
iv. a transmitting unit (75) transmitting the control data to a programmable control unit (80) of the personal device (25),
c. wherein the personal device (25):
(1) includes a programmable control unit (80) controlling functions of the personal device (25) in accordance with the control data, (2) transmits the control data to the control unit (80) of the personal device (25) only if the integrity of the control data set (200) is established by the check unit (70), and (3) executes, in the control unit (80), the control of functions of the personal device (20) on the basis of the control data received from the collection unit (20), and further wherein:

i. the source unit (15) generates and transmits a supplemental control data set and a supplemental check datum having an urgency indicator after a transmission of the control data set, and ii. the collection unit (20) interrupts the processing of the control data set (200) if the collection unit (20) receives the supplemental control data set having the urgency indicator.

16. A system (10) for transmitting control data for a programmable personal medical device (25), including a source unit (15), a collection unit (20), a combination unit (30), and a personal device (25), a. wherein the source unit (15) includes:
   (1) a data set unit (35) generating
      i. a first control data set (200) containing control data, and
      ii. a second control data set (200) containing control data,
   (2) a check data unit (40) generating:
      i. a first check datum usable for an integrity check of the first control data set (200), and
      ii. a separate second check datum usable for an integrity check of the second control data set (200),
   (3) a transmitting unit (45) separately transmitting:
      i. the first control data set (200) and the first check datum, and
      ii. the second control data set (200) and the second check datum, to the combination unit (30), b. wherein the combination unit (30) includes:
   (1) a receiving unit (60') receiving the first and second control data sets (200) from the source unit (15),
   (2) a check unit (70') checking the integrity of the first and second control data sets (200) using the first check datum and the second check datum,
   (3) a storage unit (65') storing the first and second control data sets (200),
   (4) a check data unit (40') generating at least one combination check datum for a third control data set (200), wherein the third control data set (200) includes the first and second control data sets (200),
   (5) a transmitting unit (45') transmitting the third control data set (200) and the combination check datum to the collection unit (20) only if the check unit (70') verifies the integrity of the first and second control data sets (200), c. wherein the collection unit (20) includes:
   (1) a receiving unit (60) receiving the third control data set (200) and the combination check datum,
   (2) a storage unit (65) storing the third control data set (200),
   (3) a check unit (70) checking the integrity of the third control data set (200) using the combination check datum, and (4) a transmitting unit (75) transmitting the third control data set (200) to a programmable control unit (80) of the personal device (25) only if the integrity of the third control data set (200) is established by the check unit (70), d. wherein the personal device (25):
   (1) includes a programmable control unit (80) controlling functions of the personal device (25) in accordance with the third control data set (200),
   (3) executes, in the control unit (80), the control of functions of the personal device (20) on the basis of the third control data set (200) received from the collection unit (20)$_3$ and further wherein:

i. the source unit (15) generates and transmits a fourth control data set and a fourth check datum having an urgency indicator after a transmission of the first control data set, and ii. the collection unit (20) interrupts the processing of the first control data set (200) if the collection unit (20) receives the fourth control data set having the urgency indicator.

17. A method for transmitting control data for a programmable personal medical device (25), the method including the steps of:

a. generating:
   (1) a first control data set (200) having first control data therein, and
   (2) at least one first check datum for the first control data, b. transmitting the first control data and the first check datum to a collection unit (20), wherein the collection unit (20) is:
   (1) situated separately from the personal medical device (25) within a patient device (85) assigned to the personal device (25), and
   (1) coupled to the personal medical device (25) via a wireless data connection, c. generating:
   (1) a subsequent control data set (200) having subsequent control data therein, and
   (2) at least one subsequent check datum for the subsequent control data, and
   (3) an urgency indicator, d. transmitting the subsequent control data, the subsequent check datum, and the urgency indicator to the collection unit (20), e. within the collection unit (20),
   (1) storing the transmitted first control data,
   (2) checking the integrity of the stored first control data using the first check datum, and
   (3) if the integrity of the stored first control data is verified, transmitting the first control data to a programmable control unit (80) of a personal device (25), until the collection unit (20) receives the subsequent control data, the subsequent check datum, and the urgency indicator;

e. controlling the function of the personal device (25) in accordance with the most recently transmitted control data received from the collection unit (20).

* * * * *